(12) United States Patent
Hoshino et al.

(10) Patent No.: US 9,795,549 B2
(45) Date of Patent: Oct. 24, 2017

(54) 1,2-ALKANE POLYOL-CONTAINING COMPOSITION

(71) Applicant: OSAKA ORGANIC CHEMICAL INDUSTRY LTD., Osaka-shi, Osaka (JP)

(72) Inventors: Yutaka Hoshino, Hakusan (JP); Takahiro Mukaiyama, Hakusan (JP)

(73) Assignee: OSAKA ORGANIC CHEMICAL INDUSTRY LTD., Osaka-shi (JP)

( * ) Notice: Subject to any disclaimer, the term of this patent is extended or adjusted under 35 U.S.C. 154(b) by 0 days.

(21) Appl. No.: 14/879,472

(22) Filed: Oct. 9, 2015

(65) Prior Publication Data

US 2016/0045414 A1 Feb. 18, 2016

Related U.S. Application Data

(63) Continuation of application No. PCT/JP2014/057956, filed on Mar. 24, 2014.

(30) Foreign Application Priority Data

Apr. 11, 2013 (JP) ................................ 2013-082729

(51) Int. Cl.
| | | |
|---|---|---|
| *A61K 8/34* | (2006.01) | |
| *C09D 7/12* | (2006.01) | |
| *A61K 8/49* | (2006.01) | |
| *C09D 11/38* | (2014.01) | |
| *A61Q 19/00* | (2006.01) | |
| *A61Q 5/00* | (2006.01) | |
| *C09D 201/00* | (2006.01) | |
| *C07C 29/94* | (2006.01) | |

(52) U.S. Cl.
CPC ............. *A61K 8/345* (2013.01); *A61K 8/347* (2013.01); *A61K 8/4926* (2013.01); *A61Q 5/00* (2013.01); *A61Q 19/00* (2013.01); *A61Q 19/007* (2013.01); *C07C 29/94* (2013.01); *C09D 7/12* (2013.01); *C09D 7/1233* (2013.01); *C09D 11/38* (2013.01); *C09D 201/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 4,879,107 | A | 11/1989 | Vanlerberghe et al. |
| 2011/0069108 | A1 | 3/2011 | Fukuda |

FOREIGN PATENT DOCUMENTS

| | | | |
|---|---|---|---|
| JP | 63-297312 | A | 12/1988 |
| JP | 9-227425 | A | 9/1997 |
| JP | 11-310506 | A | 11/1999 |
| JP | 11-322591 | A | 11/1999 |
| JP | 2001-72531 | A | 3/2001 |
| JP | 2003-81736 | A | 3/2003 |
| JP | 2005-298370 | A | 10/2005 |
| JP | 2008-31141 | A | 2/2008 |
| JP | 2008-156260 | A | 7/2008 |
| JP | 2008-156263 | A | 7/2008 |
| JP | 2008-297206 | A | 12/2008 |
| JP | 2011-178981 | A | 9/2011 |
| JP | 2012-120441 | A | 6/2012 |
| JP | 2012-136616 | A | 7/2012 |
| WO | 2009/133796 | A1 | 11/2009 |

OTHER PUBLICATIONS

International Search Report dated May 13, 2014, issued in Counterpart Application No. PCT/JP2014/057956 (3 pages).

*Primary Examiner* — Kristin Vajda
(74) *Attorney, Agent, or Firm* — Westerman, Hattori, Daniels & Adrian, LLP

(57) ABSTRACT

Provided is a composition containing, as an alkane polyol, a $C_{4-18}$ 1,2-alkane polyol in which the degradation over time of the $C_{4-18}$ 1,2-alkane polyol, which has inferior chemical stability and degrades easily, is suppressed, the composition being suitable for use in a cosmetic, an inkjet ink, a fiber or a coating material such as a paint. A composition containing 1,2-alkane polyol that can be used in a cosmetic, an inkjet ink, a raw material for fibers or a coating material, the alkane polyol being a $C_{4-18}$ 1,2-alkane polyol, and the composition containing a radical scavenger.

2 Claims, 2 Drawing Sheets

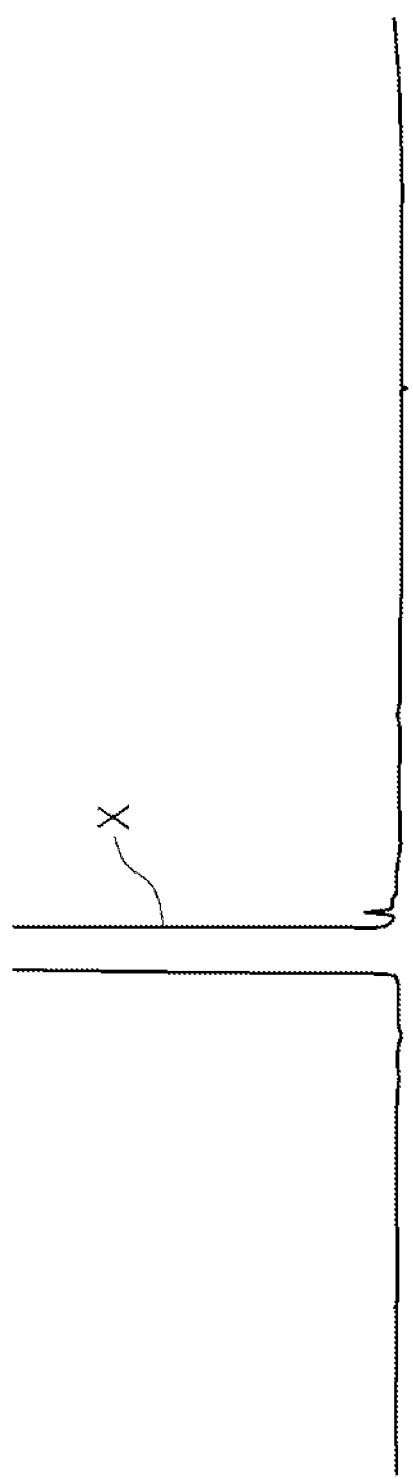
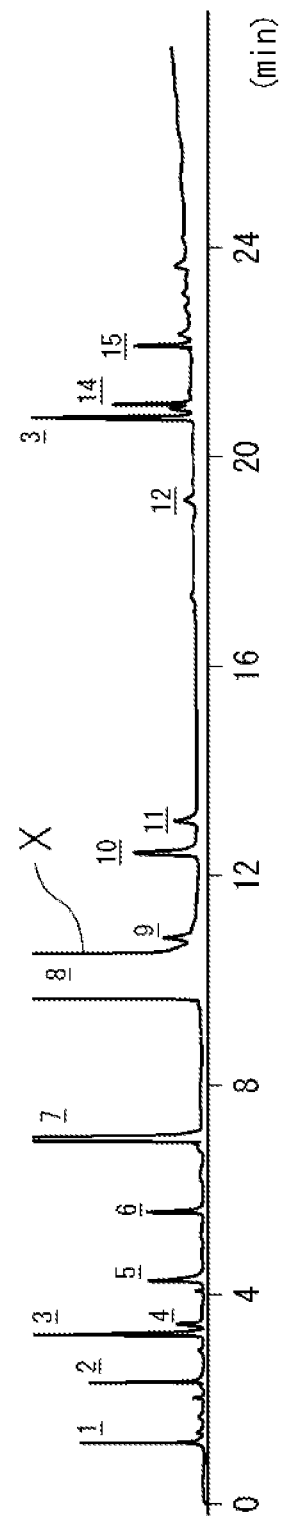
FIG. 1(a)
FIG. 1(b)

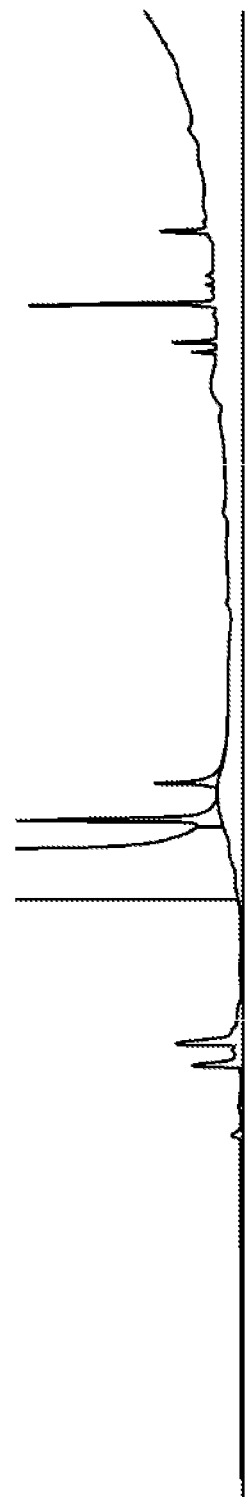
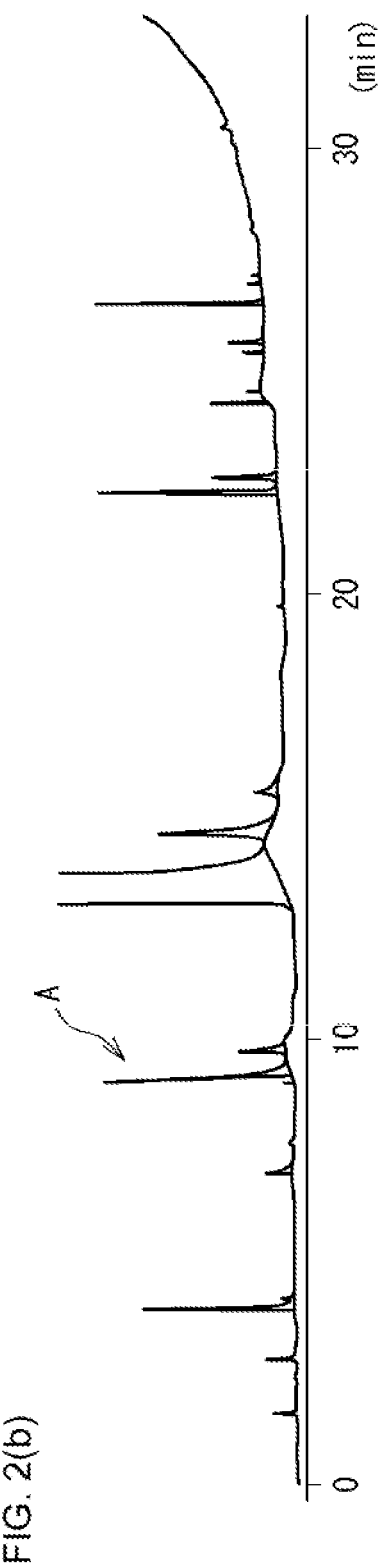
FIG. 2(a)
FIG. 2(b)

1,2-ALKANE POLYOL-CONTAINING COMPOSITION

TECHNICAL FIELD

The present invention relates to a 1,2-alkane polyol-containing composition. More specifically, the present invention relates to a 1,2-alkane polyol-containing composition which can be suitably used in cosmetics, an ink for inkjet printers, a raw material for fibers, a coating material such as a paint, and the like.

BACKGROUND ART

A 1,2-alkane polyol has been used in, for example, cosmetics, an ink for inkjet printers, a raw material for fibers, and a coating material such as a paint. However, the 1,2-alkane polyol is a compound which is easily oxidized and easily decomposed with the passage of time. When the 1,2-alkane polyol is decomposed, an acid and an aldehyde are generated from the 1,2-alkane polyol. Therefore, it has been apprehended that coloring, smell, stimulatory and the like are emanated from the acid and the aldehyde.

As a method for stabilizing ethylene glycol which one of alkane polyols, there have been proposed a method for adding a carboxylic acid derivative to ethylene glycol (see, for example. Patent Literature 1), a method for adding a thiazoline derivative to ethylene glycol (see, for example, Patent Literature 2), and the like.

In recent years, it has been desired to inhibit deterioration of a 1,2-alkane polyol having 4 to 18 carbon atoms, which is chemically unstable and easily deteriorates with the passage of time, and to develop a composition containing a 1,2-alkane polyol having 4 to 18 carbon atoms other than ethylene glycol, which can be suitably used in cosmetics, an ink for inkjet printers, a raw material for fibers, a coating material such as a paint, and the like.

PRIOR ART LITERATURES

Patent Literatures

Patent Literature 1: Japanese Unexamined Patent Publication No. Hei 9-227425

Patent Literature 2: Japanese Unexamined Patent Publication No. 2008-156263

SUMMARY OF THE INVENTION

Problems to be Solved by the Invention

The present invention has been accomplished in view of the above-mentioned prior arts. An object of the present invention is to provide a composition containing a 1,2-alkane polyol having 4 to 18 carbon atoms, which is chemically unstable and easily degraded with the passage of time, and to provide a composition containing a 1,2-alkane polyol having 4 to 18 carbon atoms, which can be suitably used in cosmetics, an ink for inkjet printers, a raw material for fibers, a coating material such as a paint, and the like.

Means for Solving the Problems

The present invention relates to
(1) a 1,2-alkane polyol-containing composition used in cosmetics, an ink for inkjet printers, a raw material for fibers or a coating material, wherein the above-mentioned 1,2-alkane polyol is a 1,2-alkane polyol having 4 to 18 carbon atoms, and the composition contains a radical scavenger; and
(2) the 1,2-alkane polyol-containing composition according to the above-mentioned item (1), wherein the radical scavenger is at least one member selected from the group consisting of a phenolic radical scavenger, a tetramethylpiperidineoxyl radical scavenger, a quinone radical scavenger, an amine radical scavenger, an organic acid radical scavenger and a phenothiazine radical scavenger.

Incidentally, in the present specification, the term "1,2-alkane polyol" means an alkane polyol having hydroxyl groups at the positions of at least position 1 and position 2 of the 1,2-alkane polyol.

Effects of the Invention

According to the present invention, there is provided a composition containing a 1,2-alkane polyol having 4 to 18 carbon atoms, which inhibits deterioration of the 1,2-alkane polyol having 4 to 18 carbon atoms, being poor in chemical stability and easily deteriorates with the passage of time, and which can be suitably used in cosmetics, an ink for inkjet printers, a raw material for fibers, a coating material such as a paint, and the like.

According to the 1,2-alkane polyol-containing composition of the present invention, since deterioration of a 1,2-alkane polyol having 4 to 18 carbon atoms with the passage of time is inhibited, generation of coloring, smell, stimulatory and the like which are emanated from an acid and an aldehyde generated by the decomposition of the 1,2-alkane polyol having 4 to 18 carbon atoms can be inhibited.

BRIEF DESCRIPTION OF DRAWINGS

FIG. 1(a) is a drawing showing results when 1,2-octanediol was analyzed by gas chromatography in Reference Example 1, and FIG. 1(b) is a drawing showing results when 1,2-octanediol to which an accelerated deterioration test was conducted was analyzed by gas chromatography in Reference Example 1.

FIG. 2(a) is a drawing showing results when 1,2-hexanediol was analyzed by gas chromatography in Reference Example 2, and FIG. 2(b) is a drawing showing results when 1,2-hexanediol to which an accelerated deterioration test was conducted was analyzed by gas chromatography in Reference Example 2.

MODE FOR CARRYING OUT THE INVENTION

As mentioned above, the 1,2-alkane polyol-containing composition of the present invention is a composition containing a 1,2-alkane polyol, in which the above-mentioned 1,2-alkane polyol is a 1,2-alkane polyol having 4 to 18 carbon atoms, and the composition contains a radical scavenger.

Since the composition of the present invention contains the above-mentioned components, deterioration of a 1,2-alkane polyol having 4 to 18 carbon atoms can be inhibited, and temporal stability of the 1,2-alkane polyol can be remarkably improved.

The 1,2-alkane polyol having 4 to 18 carbon atoms includes, for example, an alkane diol having 4 to 18 carbon atoms, an alkane triol having 4 to 18 carbon atoms and the like, and the present invention is not limited only to those exemplified ones. These 1,2-alkane polyols can be used alone, or at least two kinds thereof can be used in combination.

The 1,2-alkanediol having 4 to 18 carbon atoms includes, for example, 1,2-butanediol, 1,2-pentanediol, 1,2-hexanediol, 1,2-heptanediol, 1,2-octanediol, 1,2-nonanediol, 1,2-decanediol, 1,2-undecanediol, 1,2-dodecanediol, 1,2-tridecanediol, 1,2-tetradecanediol, 1,2-pentadecanediol, 1,2-hexadecanediol, 1,2-heptadecanediol, 1,2-octadecanediol and the like, and the present invention is not limited only to those exemplified ones. These 1,2-alkanediols can be used alone, or at least two kinds thereof can be used in combination.

The 1,2-alkanetriol having 4 to 18 carbon atoms includes, for example, 1,2,3-butanetriol, 1,2,4-butanetriol, 1,2,3-pentanetriol, 1,2,4-pentanetriol, 1,2,6-hexanetriol, 2-methyl-1,2,3-propanetriol, 2-ethylbutane-1,2,3-triol, 2-methyl-2-hydroxymethylpropane-1,3-diol, 2-ethyl-2-hydroxymethylpropane-1,3-diol and the like, and the present invention is not limited only to those exemplified ones. These 1,2-alkanetriols can be used alone, or at least two kinds of thereof can be used in combination.

The radical scavenger includes, for example, a phenolic radical scavenger, a tetramethylpiperidineoxyl radical scavenger, a quinone radical scavenger, an amine radical scavenger, an organic acid radical scavenger, a phenothiazine radical scavenger and the like, and the present invention is not limited only to those exemplified ones. These radical scavengers can be used alone, or at least two kinds of thereof can be used in combination.

The phenolic radical scavenger includes, for example, 2-methylphenol, 2-ethylphenol, 2-propylphenol, 2-isopropylphenol, 2-(1,1-dimethyl)propylphenol, 2-butylphenol, 2-tert-butylphenol, 2-pentylphenol, 2-neopentylphenol, 2-hexylphenol, 2-methoxyphenol, 2-phenylphenol, 2-(1-naphthyl)phenol, 2-(2-naphthyl)phenol, 2-hydroxyphenol, 2-aminophenol, 2-nitrophenol, 2-sulfanylphenol, 2-aminophenol, 2-formylphenol, 2-acetylphenol, 4-methylphenol, 4-ethylphenol, 4-propylphenol, 4-isopropylphenol, 4-(1,1-dimethyl)propylphenol, 4-butylphenol, 4-tert-butylphenol, 4-pentylphenol, 4-neopentylphenol, 4-hexylphenol, 4-methoxyphenol, 4-phenylphenol, 4-(1-naphthyl)phenol, 4-(2-naphthyl)phenol, 4-hydroxyphenol, 4-aminophenol, 4-nitrophenol, 4-sulfanylphenol, 4-aminophenol, 4-formylphenol, 4-acetylphenol, 6-methylphenol, 6-ethylphenol, 6-propylphenol, 6-isopropylphenol, 6-(1,1-dimethyl)propylphenol, 6-butylphenol, 6-tert-butylphenol, 6-pentylphenol, 6-neopentylphenol, 6-hexylphenol, 6-methoxyphenol, 6-phenylphenol, 6-(1-naphthyl)phenol, 6-(2-naphthyl)phenol, 6-hydroxyphenol, 6-aminophenol, 6-nitrophenol, 6-sulfanylphenol, 6-amninophenol, 6-formylphenol, 6-acetylphenol, 2,4-dimethylphenol, 2,4-diethylphenol, 2,4-dipropylphenol, 2,4-diisopropylphenol, 2,4-di(1,1-dimethyl)propylphenol, 2,4-dibutylphenol, 2,4-ditert-butylphenol, 2,4-dipentylphenol, 2,4-dineopentylphenol, 2,4-dihexylphenol, 2,4-dimethoxyphenol, 2,4-diphenylphenol, 2,4-di(1-naphthyl)phenol, 2,4-di(2-naphthyl)phenol, 2,4-dihydroxyphenol, 2,4-diaminophenol, 2,4-dinitrophenol, 2,4-disulfanylphenol, 2,4-diaminophenol, 2,4-diformylphenol, 2,4-diacetylphenol, 2,6-dimethylphenol, 2,6-diethylphenol, 2,6-dipropylphenol, 2,6-diisopropylphenol, 2,6-di(1,1-dimethyl)propylphenol, 2,6-dibutylphenol, 2,6-ditert-butylphenol, 2,6-ditert-butyl-4-methylphenol, 2,6-dipentylphenol, 2,6-dineopentylphenol, 2,6-dihexylphenol, 2,6-dimethoxyphenol, 2,6-diphenylphenol, 2,6-di(I-naphthyl)phenol, 2,6-di(2-naphthyl)phenol, 2,6-dihydroxyphenol, 2,6-diaminophenol, 2,6-dinitrophenol, 2,6-disulfanylphenol, 2,6-diaminophenol, 2,6-diformylphenol, 2,6-diacetylphenol, 2,4,6-trimethylphenol, 2,4,6-triethylphenol, 2,4,6-tripropylphenol, 2,4,6-triisopropylphenol, 2,4,6-tri(1,1-dimethyl)propylphenol, 2,4,6-tributylphenol, 2,4,6-tritert-butylphenol, 2,4,6-tripentylphenol, 2,4,6-trineopentylphenol, 2,4,6-trihexylphenol, 2,4,6-trimethoxyphenol, 2,4,6-triphenylphenol, 2,4,6-tri(1-naphthyl)phenol, 2,4,6-tri(2-naphthyl)phenol, 2,4,6-trihydroxyphenol, 2,4,6-triaminophenol, 2,4,6-trinitrophenol, 2,4,6-trisulfanylphenol, 2,4,6-triaminophenol, 2,4,6-triformylphenol, 2,4,6-triacetylphenol, 2-methyl-4-tert-butylphenol, 2-ethyl-4-tert-butylphenol, 2-propyl-4-tert-butylphenol, 2-isopropyl-4-tert-butylphenol, 2-(1,1-dimethyl)propyl-4-tert-butylphenol, 2-butyl-4-tert-butylphenol, 2-pentyl-4-tert-butylphenol, 2-neopentyl-4-tert-butylphenol, 2-hexyl-4-tert-butylphenol, 2-methoxy-4-tert-butylphenol, 2-phenyl-4-tert-butylphenol, 2-(1-naphthyl)-4-tert-butylphenol, 2-(2-naphthyl)-4-tert-butylphenol, 2-hydroxy-4-tert-butylphenol, 2-amino-4-tert-butylphenol, 2-nitro-4-tert-butylphenol, 2-sulfanyl-4-tert-butylphenol, 2-formyl-4-tert-butylphenol, 2-acetyl-4-tert-butylphenol, 2-methyl-6-tert-butylphenol, 2-ethyl-6-tert-butylphenol, 2-propyl-6-tert-butylphenol, 2-isopropyl-6-tert-butylphenol, 2-(1,1-dimethyl)propyl-6-tert-butylphenol, 2-butyl-6-tert-butylphenol, 2-pentyl-6-tert-butylphenol, 2-neopentyl-6-tert-butylphenol, 2-hexyl-6-tert-butylphenol, 2-methoxy-6-tert-butylphenol, 2-phenyl-6-tert-butylphenol, 2-(1-naphthyl)-6-tert-butylphenol, 2-(2-naphthyl)-6-tert-butylphenol, 2-hydroxy-6-tert-butylphenol, 2-amino-6-tert-butylphenol, 2-nitro-6-tert-butylphenol, 2-sulfanyl-6-tert-butylphenol, 2-formyl-6-tert-butylphenol, 2-acetyl-6-tert-butylphenol, 2,6-dimethyl-4-tert-butylphenol.

2-ethyl-4-tert-butyl-6-methylphenol, 2-propyl-4-tert-butyl-6-methylphenol, 2-isopropyl-4-tert-butyl-6-methylphenol, 2-(1,1-dimethyl)propyl-4-tert-butyl-6-methylphenol, 2-butyl-4-tert-butyl-6-methylphenol, 2-pentyl-4-tert-butyl-6-methylphenol, 2-neopentyl-4-tert-butyl-6-methylphenol, 2-hexyl-4-tert-butyl-6-methylphenol, 2-methoxy-4-tert-butyl-6-methylphenol, 2-phenyl-4-tert-butyl-6-methylphenol, 2-(1-naphthyl)-4-tert-butyl-6-methylphenol, 2-(2-naphthyl)-4-tert-butyl-6-methylphenol, 2-hydroxy-4-tert-butyl-6-methylphenol, 2-amino-4-tert-butyl-6-methylphenol, 2-nitro-4-tert-butyl-6-methylphenol, 2-sulfanyl-4-tert-butylphenol, 2-formyl-4-tert-butyl-6-methylphenol, 2-acetyl-4-tert-butyl-6-methylphenol, 2,4-dimethyl-6-tert-butylphenol, 2-ethyl-6-tert-butyl-4-methylphenol, 2-propyl-6-tert-butyl-4-methylphenol, 2-isopropyl-6-tert-butyl-4-methylphenol, 2-(1,1-dimethyl)propyl-6-tert-butyl-4-methylphenol, 2-butyl-6-tert-butyl-4-methylphenol, 2-pentyl-6-tert-butyl-4-methylphenol, 2-neopentyl-6-tert-butyl-4-methylphenol, 2-hexyl-6-tert-butyl-4-methylphenol, 2-methoxy-6-tert-butyl-4-methylphenol, 2-phenyl-6-tert-butyl-4-methylphenol, 2-(1-naphthyl)-6-tert-butyl-4-methylphenol, 2-(2-naphthyl)-6-tert-butyl-4-methylphenol, 2-hydroxy-6-tert-butyl-4-methylphenol, 2-amino-6-tert-butyl-4-methylphenol, 2-nitro-6-tert-butyl-4-methylphenol, 2-sulfanyl-6-tert-butyl-4-methylphenol, 2-formyl-6-tert-butyl-4-methylphenol, 2-acetyl-6-tert-butyl-4-methylphenol, 4-methyl-2,6-ditert-butylphenol, 4-ethyl-2,6-ditert-butylphenol, 4-propyl-2,6-ditert-butylphenol, 4-isopropyl-2,6-ditert-butylphenol, 4-(1,1-dimethyl)propyl-2,6-ditert-butylphenol, 4-butyl-2,6-ditert-butylphenol, 2,4,6-tritert-butylphenol, 4-pentyl-2,6-ditert-butylphenol, 4-neopentyl-2,6-ditert-butylphenol, 4-hexyl-2,6-ditert-butylphenol, 4-methoxy-2,6-ditert-butylphenol, 4-methoxy-3-tert-butylphenol, 4-phenyl-2,6-ditert-butylphenol, 4-(1-naphthyl)-2,6-ditert-butylphenol, 4-(2-naphthyl)-2,6-ditert-butylphenol, 4-hydroxy-2,6-ditert-butylphenol, 4-amino-2,6-ditert-butylphenol, 4-nitro-2,6-ditert-butylphenol, 4-sulfanyl-2,6-ditert-butylphenol, 4-amino-2,6-ditert-butylphenol, 4-formyl-2,6-ditert-butylphenol, 4-acetyl-2,6-ditert-butylphenol, 2-methyl-4,6-ditert-butylphenol, 2-ethyl-4,6-ditert-butylphenol, 2-propyl-4,6-ditert-butylphenol, 2-isopropyl-4,6-ditert-butylphenol, 2-(1,1-dimethyl)propyl-4,6-ditert-butylphenol, 2-butyl-4,6-ditert-butylphenol, 2-tert-butyl-4,6-ditert-butylphenol, 2-pentyl-4,6-ditert-butylphenol, 2-neopentyl-4,6-ditert-butylphenol, 2-hexyl-4,6-ditert-butylphenol, 2-methoxy-4,6-ditert-butylphenol, 2-phenyl-4,6-ditert-butylphenol, 2-(1-naphthyl)-4,6-ditert-butylphenol, 2-(2-naphthyl)-4,6-ditert-butylphenol, 2-hydroxy-4,6-ditert-butylphenol, 2-amino-4,6-ditert-butylphenol, 2-nitro-4,6-ditert-butylphenol, 2-sulfanyl-4,6-ditert-butylphenol, 2-amino-4,6-ditert-butylphenol, 2-formyl-4,6-ditert-butylphenol, 2-acetyl-4,6-ditert-butylphenol, 2,4-dimethyl-6-ethylphenol, 2,4-dimethyl-6-propylphenol, 2,4-dimethyl-6-isopropylphenol, 2,4-dimethyl-6-(1,1-dimethyl)propylphenol, 2,4-dimethyl-6-butylphenol, 2,4-dimethyl-6-tert-butylphenol, 2,4-dimethyl-6-pentylphenol, 2,4-dimethyl-6-neopentylphenol, 2,4-dimethyl-6-hexylphenol, 2,4-dimethyl-6-methoxyphenol, 2,4-dimethyl-6-phenylphenol, 2,4-dimethyl-6-(1-naphthyl)phenol, 2,4-dimethyl-6-(2-naphthyl)phenol, 2,4-dimethyl-6-hydroxyphenol, 2,4-dimethyl-6-aminophenol, 2,4-dimethyl-6-nitrophenol, 2,4-dimethyl-6-sulfanylphenol, 2,4-dimethyl-6-aminophenol, 2,4-dimethyl-6-formylphenol, 2,4-dimethyl-6-acetylphenol.

2,6-dimethyl-4-ethylphenol, 2,6-dimethyl-4-propylphenol, 2,6-dimethyl-4-isopropylphenol, 2,6-dimethyl-4-(1,1-dimethyl)propylphenol, 2,6-dimethyl-4-butylphenol, 2,6-dimethyl-4-tert-butylphenol, 2,6-dimethyl-4-pentylphenol, 2,6-dimethyl-4-neopentylphenol, 2,6-dimethyl-4-hexylphenol, 2,6-dimethyl-4-methoxyphenol, 2,6-dimethyl-4-phenylphenol, 2,6-dimethyl-4-(1-naphthyl)phenol, 2,6-dimethyl-4-(2-naphthyl)phenol, 2,6-dimethyl-4-hydroxyphenol, 2,6-dimethyl-4-aminophenol, 2,6-dimethyl-4-nitrophenol, 2,6-dimethyl-4-sulfanylphenol, 2,6-dimethyl-4-aminophenol, 2,6-dimethyl-4-formylphenol, 2,6-dimethyl-4-acetylphenol, pyrogallol, resorcinol, 4-octylphenol, shikonin, propyl gallate, octyl gallate, methylparaben, ethylparaben, propylparaben, isopropylparaben, butylparaben, isobutylparaben, benzylparaben, benzoic acid, salicylic acid, epicatechin, epicatechin gallate, epigallocatechin gallate, epigallocatechin, catechin, catechin gallate, gallocatechin gallate, gallocatechin, galvinoxyl free radical, bisphenol, bisphenol A, bisphenol S, bisphenol P, bisphenol AF, bisphenol M, 4,4'-isopropylidenebis(2,6-dimethylphenol), 2,2-bis(4-hydroxyphenyl)butane, 1,1-bis(4-hydroxyphenyl)cyclohexane, 2,2'-oxydiphenol, 4,4'-ethylidenebisphenol, α-tocopherol, β-tocopherol, γ-tocopherol, δ-tocopherol and the like, and the present invention is not limited only to those exemplified ones. These phenolic radical scavengers can be used alone, or at least two kinds of thereof can be used in combination.

The tetramethylpiperidineoxyl radical scavenger includes, for example, 2,2,6,6-tetramethylpiperidine-1-oxyl, 4-hydroxy-2,2,6,6-tetramethylpiperidine-1-oxyl, 4-amino-2,2,6,6-tetramethylpiperidine-1-oxyl, 4-cyano-2,2,6,6-tetramethylpiperidine-1-oxyl, 4-benzoxy-2,2,6,6-tetramethylpiperidine-1-oxyl, 4-methoxy-2,2,6,6-tetramethylpiperidine-1-oxyl, 4-oxo-2,2,6,6-tetramethylpiperidine-1-oxyl, 4-acetamido-2,2,6,6-tetramethylpiperidine-1-oxyl and the like, and the present invention is not limited only to those exemplified ones. These tetramethylpiperidineoxyl radical scavengers can be used alone, or at least two kinds of thereof can be used in combination.

The quinone radical scavenger includes, for example, hydroquinone, methylhydroquinone, ethylhydroquinone, propylhydroquinone, butylhydroquinone, pentylhydroquinone, hexylhydroquinone, tert-butylhydroquinone, hydroxyhydroquinone, 2,5-dimethylhydroquinone, 2,5-diethylhydroquinone, 2,5-dipropylhydroquinone, 2,5-dibutylhydroquinone, 2,5-dipentylhydroquinone, 2,5-dihexylhydroquinone, 2,5-ditert-butylhydroquinone, 2,5-dihydroxyhydroquinone, 2,5-diphenylhydroquinone, naphthoquinone, benzoquinone, o-benzoquinone, p-benzoquinone, methyl-p-benzoquinone, ethyl-p-benzoquinone, propyl-p-benzoquinone, butyl-p-benzoquinone, pentyl-p-benzoquinone, hexyl-p-benzoquinone, tert-butyl-p-benzoquinone, 2,5-dimethyl-p-benzoquinone, 2,5-diethyl-p-benzoquinone, 2,5-dipropyl-p-benzoquinone, 2,5-dibutyl-p-benzoquinone, 2,5-dipentyl-p-benzoquinone, 2,5-dihexyl-p-benzoquinone, 2,5-ditert-butyl-p-benzoquinone, 2,5-diphenyl-p-benzoquinone, 3-methyl-o-benzoquinone, 3-ethyl-o-benzoquinone, 3-tert-butyl-o-benzoquinone, 4-methyl-o-benzoquinone, 4-tert-butyl-o-benzoquinone, 2-methyl-3-phytyl-1,4-naphthoquinone, 2-farnesyl-3-methyl-1,4-naphthoquinone and the like, and the present invention is not limited only to those exemplified ones. These quinone radical scavengers can be used alone, or at least two kinds of thereof can be used in combination.

The amine radical scavenger includes, for example, diphenylamine, N,N'-diphenyl-1,4-phenylenediamine, N,N'-di-2-naphthyl-1,4-phenylenediamine, phenylisopropyl-p-phenylenediamine, N-isopropyl-N'-phenyl-p-phenylenediamine, sodium ethylenediaminetetraacetate and the like, and the present invention is not limited only to those exemplified ones. These amine radical scavengers can be used alone, or at least two kinds of thereof can be used in combination.

The organic acid radical scavenger includes, for example, ascorbic acid, erythorbic acid, citric acid, maleic acid, malonic acid, succinic acid, fumaric acid, cephalin, hexametaphosphate, phytic acid, ethylenediaminetetraacetic acid and the like, and the present invention is not limited only to those exemplified ones. These organic acid radical scavengers can be used alone, or at least two kinds of thereof can be used in combination.

The phenothiazine radical scavenger includes, for example, phenothiazine and the like, and the present invention is not limited only to those exemplified ones.

Among the radical scavengers, the phenolic radical scavenger, the tetramethylpiperidineoxyl radical scavenger, the amine radical scavenger and the quinone radical scavenger are preferable; the phenolic radical scavenger, the tetramethylpiperidineoxyl radical scavenger and the amine radical scavenger are more preferable; the tetramethylpiperidineoxyl radical scavenger and the amine radical scavenger are further preferable; 2,6-ditert-butyl-4-methylphenol and 4-hydroxy-2,2,6,6-tetramethylpiperidine-1-oxyl are furthermore preferable; and 2,6-ditert-butyl-4-methylphenol is particularly preferable, since those radical scavengers are excellent in inhibition of deterioration of a 1,2-alkane polyol having 4 to 18 carbon atoms with the passage of time. Incidentally, these radical scavengers can be used alone, or at least two kinds of thereof can be used in combination.

The amount of the radical scavenger per 1 g of an alkane polyol cannot be absolutely determined, because the amount differs depending on the kind of the radical scavenger. The amount of the radical scavenger per 1 g of an alkane polyol is preferably not less than 0.003 mg, more preferably not less than 0.005 mg, and furthermore preferably not less than 0.01 mg from the viewpoint of sufficient inhibition of deterioration of the alkane polyol, and is preferably not more than 10 mg, more preferably not more than 5 mg, and furthermore preferably not more than 3 mg from the viewpoint of sufficient inhibition of deterioration of the alkane polyol.

The 1,2-alkane polyol-containing composition of the present invention can be easily prepared by mixing a 1,2-alkane polyol having 4 to 18 carbon atoms with a radical scavenger.

Incidentally, the 1,2-alkane polyol-containing composition of the present invention may contain, for example, additives such as a solvent, a thickener, a colorant, a perfume, a deodorant, a pH regulator, a chelating agent, a filler, an antiseptic agent, a surfactant, a defoaming agent, a rust inhibitor, a polymerization inhibitor, an ultraviolet absorbing agent and an ultraviolet stabilizer within a scope which would not hinder an object of the present invention.

The 1,2-alkane polyol-containing composition of the present invention as obtained in the above is excellent in chemical stability, inhibits deterioration of a 1,2-alkane polyol having 4 to 18 carbon atoms with the passage of time, and moreover inhibits the generation of turbidity, coloring, smell, stimulatory and the like. Therefore, the 1,2-alkane polyol-containing composition can be suitably used as a raw material of cosmetics, an ink for inkjet printers, fibers, a coating material such as a paint, and the like, for which inhibition of deterioration with the passage of time is required.

Incidentally, when the 1,2-alkane polyol-containing composition of the present invention is used in cosmetics, the composition can be used as a moisturizing agent, an antibacterial agent and the like. When the 1,2-alkane polyol-containing composition of the present invention is used in an ink for inkjet printers or a coating material such as a paint, the composition can be used as a solvent, a lubricant, a penetrating agent, a raw material of a vehicle and the like. When the 1,2-alkane polyol-containing composition of the present invention is used for a fiber, the composition can be used as a raw material of a polyether, a raw material of a polyurethane, a raw material of a polyester and the like, which are raw materials for fibers.

EXAMPLES

Next, the present invention will be more specifically described in accordance with the following working examples. However, the present invention is not limited only to those working examples.

Reference Example 1

As a 1,2-alkane polyol, 1,2-octanediol was used. The gas chromatography of 1,2-octanediol was examined by using a gas chromatography analyzing apparatus commercially available from Shimadzu Corporation under the product number of GC-2010 (column: Phenomenex ZB-5 having a diameter of 0.32 mm, a length of 30 m and a film thickness of 1.0 μm). Its result is shown in FIG. 1(a).

Next, a screw tube was charged with 20 g of the 1,2-octanediol in the air, and this screw tube was allowed to stand in a thermostatic oven of 80° C. for 80 hours, to carry out an accelerated deterioration test of the 1,2-octanediol. Thereafter, gas chromatography of the 1,2-octanediol was examined in the same manner as in the above. Its result is shown in FIG. 1(b).

In FIG. 1, the mark "X" denotes a peak of 1,2-octanediol.

From the results shown in FIG. 1, it can be seen that impurities are generated when deterioration of 1,2-octanediol is accelerated by heating the 1,2-octanediol to 80° C. In addition, smell emanated from 1,2-octanediol to which the accelerated deterioration test was conducted, and turbidity was observed in the 1,2-octanediol when the 1,2-octanediol was cooled to room temperature.

Example 1

As a 1,2-alkane polyol, 1,2-octanediol was used. A mixture was obtained by mixing 20 g of 1,2-octanediol with 20 mg of methylhydroquinone. The gas chromatography of the mixture obtained in the above was examined by using a gas chromatography analyzing apparatus commercially available from Shimadzu Corporation under the product number of GC-2010 (column: Phenomenex ZB-5 having a diameter of 0.32 mm, a length of 30 m and a film thickness of 1.0 μm), to determine the content of impurities in the mixture.

Incidentally, the content of impurities in the mixture was obtained from the equation:

[Content of impurities(ppm)]={[Area of impurities in gas chromatography]÷[Area of 1,2-octanediol in gas chromatography]}×$10^6$.

As a result, it was confirmed that the content of impurities in the mixture was detection limit (0.01 ppm, hereinafter referred to the same) or less.

Next, a screw tube was charged with the mixture obtained in the above. This screw tube was allowed to stand in a thermostatic oven of 80° C. for 80 hours, to carry out an accelerated deterioration test of the mixture. Thereafter, the mixture was examined by using a gas chromatography analyzing apparatus commercially available from Shimadzu Corporation under the product number of GC-2010 (column: Phenomenex ZB-5 having a diameter of 0.32 mm, a length of 30 m and a film thickness of 1.0 μm), to determine the content of impurities in the mixture.

Incidentally, the content of impurities in the 1,2-butanediol was obtained from the equation:

[Content of impurities(ppm)]={[Area of impurities in gas chromatography]÷[Area of 1,2-octanediol in gas chromatography]}×$10^6$.

As a result, it was confirmed that the content of impurities in the mixture after the accelerated deterioration test was detection limit or less, and that generation of impurities was efficiently inhibited.

Example 2

As a 1,2-alkane polyol, 1,2-octanediol was used. A mixture was obtained by mixing 20 g of 1,2-octanediol with 20 mg of 2,6-ditert-butyl-4-methylphenol. The content of impurities in the mixture obtained in the above was determined in the same manner as in Example 1. As a result, it was confirmed that the content of impurities in the mixture was detection limit or less.

Next, a screw tube was charged with the mixture obtained in the above. This screw tube was allowed to stand in a thermostatic oven of 80° C. for 80 hours, to carry out an accelerated deterioration test of the mixture. Thereafter, the mixture was analyzed by gas chromatography in the same manner as in Example 1, and the content of impurities in the mixture was determined. As a result, the content of impurities in the mixture after the accelerated deterioration test was detection limit or less. From this fact, it was confirmed that generation of impurities was efficiently inhibited.

Example 3

As a 1,2-alkane polyol, 1,2-octanediol was used. A mixture was obtained by mixing 20 g of 1,2-octanediol with 20 mg of 2,6-ditert-butyl-4-methylphenol. The content of impurities in the mixture obtained in the above was determined in the same manner as in Example 1. As a result, it was confirmed that the content of impurities in the mixture was detection limit or less.

Next, a screw tube was charged with the mixture obtained in the above. This screw tube was allowed to stand in a thermostatic oven of 80° C. for 60 hours, to carry out an accelerated deterioration test of the mixture. Thereafter, the mixture was analyzed by gas chromatography, and the content of impurities denoted by the mark "3" in FIG. 1 in the mixture was determined.

Incidentally, the mixture was analyzed by using a gas chromatography analyzing apparatus commercially available from Shimadzu Corporation under the product number of GC-2010 (column: Phenomenex ZB-5 having a diameter of 0.32 mm, a length of 30 m and a film thickness of 1.0 μm), and the content of impurities denoted by the mark "3" in FIG. 1 in the mixture was obtained from the equation:

[Content of impurities denoted by the mark"3" in FIG. 1 (ppm)]={[Area of impurities denoted by the mark"3" in FIG. 1 in gas chromatography]+[Area of 1,2-octanediol in gas chromatography]}×10$^6$.

As a result, it was confirmed that the content of impurities in the mixture after the accelerated deterioration test was 83 ppm, and that generation of impurities was efficiently inhibited.

Example 4

A mixture was prepared in the same manner as in Example 3, except that 1 mg of 4-acetamido-2,2,6,6-tetramethylpiperidine-1-oxyl was used in place of 2,6-ditert-butyl-4-methylphenol used in Example 3. The content of impurities in the mixture obtained in the above was determined in the same manner as in Example 1. As a result, it was confirmed that the content of impurities in the mixture was detection limit or less.

Next, an accelerated deterioration test of the mixture obtained in the above was carried out by using the mixture in the same manner as in Example 3.

As a result, the content of impurities in the mixture after the accelerated deterioration test was 84 ppm, and that generation of impurities was efficiently inhibited.

Comparative Example 1

In Example 3, 2,6-ditert-butyl-4-methylphenol was not used, and only 20 g of 1,2-octanediol was used. The content of impurities in this 1,2-octanediol was determined in the same manner as in Example 1. As a result, it was confirmed that the content of impurities was detection limit or less.

Next, an accelerated deterioration test of the 1,2-octanediol was carried out in the same manner as Example 3. As a result, it was confirmed that the content of impurities in 1,2-octanediol after the accelerated deterioration test was 848 ppm, and that the impurities were generated in a large amount.

Examples 5 to 10 and Comparative Example 2

As a 1,2-alkane polyol, 1,2-octanediol was used. A mixture was obtained by mixing 20 g of 1,2-octanediol with 4-acetamido-2,2,6,6-tetramethylpiperidine-1-oxyl.

The amount of 4-acetamido-2,2,6,6-tetramethylpiperidine-1-oxyl was adjusted to 1 mg in Example 5, 5.06 mg in Example 6, 10.08 mg in Example 7, 50.42 mg in Example 8, 201.2 mg in Example 9, and 394.3 mg in Example 10.

The content of impurities in the mixture obtained in the above was determined in the same manner as in Example 1. As a result, it was confirmed that the content of impurities in the mixture was 101 ppm in all of Examples 5 to 10.

Next, a screw tube was charged with the mixture obtained in the above. This screw tube was allowed to stand in a thermostatic oven of 80° C. for 106 hours, to carry out an accelerated deterioration test of the mixture. Thereafter, the mixture was analyzed by gas chromatography, and the content of impurities denoted by the mark "3" in FIG. 1 in the mixture was determined.

In addition, in Comparative Example 2, 4-acetamido-2,2,6,6-tetramethylpiperidine-1-oxyl, which was used in Example 5, was not used, and only 20 g of 1,2-octanediol was used. The content of impurities in this 1,2-octanediol was determined in the same manner as in Example 1. As a result, it was confirmed that the content of impurities was 101 ppm.

Next, a screw tube was charged with the 1,2-octanediol in the air. This screw tube was allowed to stand in a thermostatic oven of 80° C. for 106 hours, to carry out an accelerated deterioration test of the mixture. Thereafter, the 1,2-octanediol was analyzed by gas chromatography, and the content of impurities denoted by the mark "3" in FIG. 1 in the 1,2-octanediol was determined.

Incidentally, the mixture or 1,2-octanediol was analyzed by using a gas chromatography analyzing apparatus commercially available from Shimadzu Corporation under the product number of GC-2010 (column: Phenomenex ZB-5 having a diameter of 0.32 mm, a length of 30 m and a film thickness of 1.0 μm), and the content of impurities denoted by the mark "3" in FIG. 1 was obtained from the equation:

[Content of impurities denoted by the mark"3" in FIG. 1 (ppm)]={[Area of impurities denoted by the mark"3" in FIG. 1 in gas chromatography]+[Area of 1,2-octanediol in gas chromatography]}×10$^6$.

As a result, the content of impurities in the mixture after the accelerated deterioration test was 104 ppm in Example 5, 106 ppm in Example 6, 108 ppm in Example 7, 101 ppm in Example 8, 145 ppm in Example 9, and 182 ppm in Example 10, whereas in Comparative Example 2, the content of impurities was 2980 ppm. From this fact, it was confirmed that according to each Example, generation of impurities was more efficiently inhibited as compared with Comparative Example 2.

Examples 11 to 15 and Comparative Example 3

As a 1,2-alkane polyol, 1,2-octanediol was used. A mixture was obtained by mixing 20 g of 1,2-octanediol with 4-hydroxy-2,2,6,6-tetramethylpiperidine-1-oxyl.

Incidentally, the amount of 4-hydroxy-2,2,6,6-tetramethylpiperidine-1-oxyl was adjusted to 0.5 mg in Example 11, 1 mg in Example 12, 2 mg in Example 13, 5 mg in Example 14, and 10 mg in Example 15.

The content of impurities in the mixture obtained in the above was determined in the same manner as in Example 1. As a result, it was confirmed that the content of impurities in the mixture was 84 ppm in all of Examples 11 to 15.

Next, a screw tube was charged with the mixture obtained in the above in the air. This screw tube was allowed to stand in a thermostatic oven of 80° C. for 136 hours, to carry out an accelerated deterioration test of the mixture. Thereafter, the mixture was analyzed by gas chromatography, and the content of impurities denoted by the mark "3" in FIG. 1 in the mixture was determined.

Also, in Comparative Example 3, 4-hydroxy-2,2,6,6-tetramethylpiperidine-1-oxyl, which was used in Example 11, was not used, and only 20 g of 1,2-octanediol was used. The content of impurities in this 1,2-octanediol was determined in the same manner as in Example 1. As a result, it was confirmed that the content of impurities was 84 ppm.

Next, a screw tube was charged with the 1,2-octanediol in the air. This screw tube was allowed to stand in a thermostatic oven of 80° C. for 136 hours, to carry out an accelerated deterioration test of the mixture. Thereafter, the 1,2-octanediol was analyzed by gas chromatography, and the content of impurities denoted by the mark "3" in FIG. 1 in the 1,2-octanediol was determined.

Incidentally, the mixture or 1,2-octanediol was analyzed by using a gas chromatography analyzing apparatus commercially available from Shimadzu Corporation under the product number of GC-2010 (column: Phenomenex ZB-5 having a diameter of 0.32 mm, a length of 30 m and a film thickness of 1.0 μm), and the content of impurities denoted by the mark "3" in FIG. 1 in the mixture was obtained from the equation:

[Content of impurities denoted by the mark"3" in FIG. 1 (ppm)]={[Area of impurities denoted by the mark"3" in FIG. 1 in gas chromatography]+ [Area of 1,2-octanediol in gas chromatography]) }×10$^6$.

As a result, the content of impurities in the mixture after the accelerated deterioration test was 89 ppm in Example 11, 94 ppm in Example 12, 95 ppm in Example 13, 107 ppm in Example 14, and 84 ppm in Example 15, whereas in Comparative Example 3, the content of impurities was 850 ppm. From this fact, it was confirmed that according to each Example, generation of impurities was more efficiently inhibited as compared with Comparative Example 3.

Examples 16 to 20 and Comparative Example 4

As a 1,2-alkane polyol, 1,2-octanediol was used. A mixture was obtained by mixing 20 g of 1,2-octanediol with 10 mg of hydroquinone (Example 16), 10 mg of methylhydroquinone (Example 17), 10 mg of 2,6-ditert-butyl-4-methylphenol (Example 18), 10 mg of 4-acetamido-2,2,6,6-tetramethylpiperidine-1-oxyl (Example 19), or 10 mg of 4-hydroxy-2,2,6,6-tetramethylpiperidine-1-oxyl (Example 20).

The content of impurities in the mixture obtained in the above was determined in the same manner as in Example 1. As a result, it was confirmed that the content of impurities in the mixture was 71 ppm in all of Examples 16 to 20.

Next, a screw tube was charged with the mixture obtained in the above in the air. This screw tube was allowed to stand in a thermostatic oven of 80° C. for 118 hours, to carry out an accelerated deterioration test of the mixture. Thereafter, the mixture was analyzed by gas chromatography, and the content of impurities denoted by the mark "3" in FIG. 1 in the mixture was determined.

In addition, in Comparative Example 4, hydroquinone, which was used in Example 16, was not used, and only 20 g of 1,2-octanediol was used. The content of impurities in this 1,2-octanediol was determined in the same manner as in Example 1. As a result, it was confirmed that the content of impurities was 71 ppm.

Next, a screw tube was charged with the 1,2-octanediol in the air. This screw tube was allowed to stand in a thermostatic oven of 80° C. for 118 hours, to carry out an accelerated deterioration test of the mixture. Thereafter, the 1,2-octanediol was analyzed by gas chromatography, and the content of impurities denoted by the mark "3" in FIG. 1 in the 1,2-octanediol was determined.

Incidentally, the mixture or 1,2-octanediol was analyzed by using a gas chromatography analyzing apparatus commercially available from Shimadzu Corporation under the product number of GC-2010 (column: Phenomenex ZB-5 having a diameter of 0.32 mm, a length of 30 m and a film thickness of 1.0 μm), and the content of impurities denoted by the mark "3" in FIG. 1 in the mixture was obtained from the equation:

[Content of impurities denoted by the mark"3" in FIG. 1 (ppm)]={[Area of impurities denoted by the mark"3" in FIG. 1 in gas chromatography]+ [Area of 1,2-octanediol in gas chromatography] }×10$^6$.

As a result, the content of impurities in the mixture after the accelerated deterioration test was 82 ppm in Example 16, 86 ppm in Example 17, 91 ppm in Example 18, 89 ppm in Example 19, and 71 ppm in Example 20, whereas in Comparative Example 4, the content of impurities was 3000 ppm. From this fact, it was confirmed that according to each Example, generation of impurities was more efficiently inhibited as compared with Comparative Example 4.

Examples 21 to 23

As a 1,2-alkane polyol, 1,2-octanediol was used. A mixture was obtained by mixing 20 g of 1,2-octanediol with 4-hydroxy-2,2,6,6-tetramethylpiperidine-1-oxyl.

Incidentally, the amount of 4-hydroxy-2,2,6,6-tetramethylpiperidine-1-oxyl was adjusted to 0.1 mg in Example 21, 0.2 mg in Example 22, and 0.3 mg in Example 23.

The content of impurities in the mixture obtained in the above was determined in the same manner as in Example 1. As a result, it was confirmed that the content of impurities in the mixture was 93 ppm in all of Examples 21 to 23.

Next, a screw tube was charged with the mixture obtained in the above in the air. This screw tube was allowed to stand in a thermostatic oven of 80° C. for 120 hours, to carry out an accelerated deterioration test of the mixture. Thereafter, the mixture was analyzed by gas chromatography, and the content of impurities denoted by the mark "3" in FIG. 1 in the mixture was determined.

Incidentally, the mixture was analyzed by using a gas chromatography analyzing apparatus commercially available from Shimadzu Corporation under the product number of GC-2010 (column: Phenomenex ZB-5 having a diameter of 0.32 mm, a length of 30 m and a film thickness of 1.0 μm), and the content of impurities denoted by the mark "3" in FIG. 1 in the mixture was obtained from the equation:

[Content of impurities denoted by the mark"3" in FIG. 1 (ppm)]={[Area of impurities denoted by the mark"3" in FIG. 1 in gas chromatography]+ [Area of 1,2-octanediol in gas chromatography] }×10$^6$.

As a result, the content of impurities in the mixture after the accelerated deterioration test was 214 ppm in Example 21, 97 ppm in Example 22, and 93 ppm in Example 23. From this fact, it was confirmed that according to each Example, generation of impurities was efficiently inhibited.

Reference Example 2

As a 1,2-alkane polyol, 1,2-hexanediol was used, and analyzed by gas chromatography. Its result is shown in FIG. 2(a).

Next, a screw tube was charged with 20 g of the 1,2-hexanediol in the air, and this screw tube was allowed to stand in a thermostatic oven of 800° C. for 211 hours, to carry out an accelerated deterioration test of the mixture. Thereafter, the mixture was analyzed by using a gas chromatography analyzing apparatus commercially available from Shimadzu Corporation under the product number of GC-2010 (column: Phenomenex ZB-5 having a diameter of 0.32 mm, a length of 30 m and a film thickness of 1.0 μm). Its result is shown in FIG. 2(b).

From the results shown in FIG. 2, it can be seen that impurities are generated when deterioration of 1,2-hexanediol is accelerated by heating the 1,2-hexanediol. In addition, smell emanated from 1,2-hexanediol to which the accelerated deterioration test was conducted, and turbidity was observed in the 1,2-hexanediol when the 1,2-hexanediol was cooled to room temperature.

Also, in the gas chromatograph shown in FIGS. 2(a) and (b), the amount of impurities was increased at 78.97 minutes which was denoted by arrow A. Therefore, the impurities denoted by the arrow A (hereinafter referred to as "impurity X") were focused on in the following Examples and Comparative Examples.

Examples 24 to 30 and Comparative Example 5

As a 1,2-alkane polyol, 1,2-hexanediol was used. A mixture was obtained by mixing 20 g of 1,2-hexanediol with 0.284 mg of 4-hydroxy-2,2,6,6-tetramethylpiperidine-1-oxyl (Example 24), 0.284 mg of 6-tocopherol (Example 25), 0.284 mg of 2,6-ditert-butyl-4-methylphenol (Example 26), 0.284 mug of 2,6-dimethyl-4-tert-butylphenol (Example 27), 0.284 mg of phytic acid (Example 28), 0.284 mg of propyl gallate (Example 29), or 0.284 mg of α-tocopherol (Example 30).

The content of impurities in the mixture obtained in the above was determined in the same manner as in Example 1. As a result, it was confirmed that the content of impurities in the mixture was detection limit or less.

A screw tube was charged with the mixture obtained in the above. This screw tube was allowed to stand in a thermostatic oven of 80° C. for 211 hours, to carry out an accelerated deterioration test of the mixture. Thereafter, the mixture was analyzed by gas chromatography, to determine the content of impurity X in the mixture.

In addition, in Comparative Example 5, 4-hydroxy-2,2,6,6-tetramethylpiperidine-1-oxyl, which was used in Example 24, was not used, and only 20 g of 1,2-hexanediol was used. The content of impurities in this 1,2-hexanediol was determined in the same manner as in Example 1. As a result, it was confirmed that the content of impurities was detection limit or less.

Next, an accelerated deterioration test of the 1,2-hexanediol was carried out for 211 hours, and then 1,2-hexanediol was analyzed by gas chromatography, to determine the content of impurity X in 1,2-hexanediol.

Incidentally, the mixture or 1,2-hexanediol was analyzed by using a gas chromatography analyzing apparatus commercially available from Shimadzu Corporation under the product number of GC-2010 (column: Phenomenex ZB-5 having a diameter of 0.32 nm, a length of 30 m and a film thickness of 1.0 μm), and the content of impurity X in the mixture or the 1,2-hexanediol was obtained from the equation:

[Content of impurity X(ppm)]={[Area of impurity X in gas chromatography]÷[Area of 1,2-hexanediol in gas chromatography]}×10$^6$.

As a result, the content of impurity in the mixture after the accelerated deterioration test was detection limit or less in Example 24, detection limit or less in Example 25, 169 ppm in Example 26, 477 ppm in Example 27, 503 ppm in Example 28, 540 ppm in Example 29, and 632 ppm in Example 30, whereas in Comparative Example 5, the content of impurities was 837 ppm. From these results, it can be seen that according to each Example, generation of impurities is more efficiently inhibited as compared with Comparative Example 5. In particular, according to Examples 24 and 25, since a phenolic radical scavenger or a tetramethylpiperidineoxyl radical scavenger was used as a radical scavenger, it can be seen that generation of impurities is more efficiently inhibited as compared with the other Examples and Comparative Example 5.

Examples 31 to 42 and Comparative Example 6

As a 1,2-alkane polyol, 1,2-hexanediol was used. A mixture was obtained by mixing 20 g of 1,2-hexanediol with 0.284 mg of 4-benzoxy-2,2,6,6-tetramethylpiperidine-1-oxyl (Example 31), 0.284 mg of 4-acetamido-2,2,6,6-tetramethylpiperidine-1-oxyl (Example 32), 0.284 mg of N-isopropyl-N'-phenyl-p-phenylenediamine (Example 33), 0.284 mg of 4-hydroxy-2,2,6,6-tetramethylpiperidine-1-oxyl (Example 34), 0.284 mg of 2,4-dimethyl-6-tert-butylphenol (Example 35), 0.284 mg of 2,6-ditert-butyl-4-methylphenol (Example 36), 0.284 mg of hydroquinone (Example 37), 0.284 mg of methylhydroquinone (Example 38), 0.284 mg of S-tocopherol (Example 39), 0.284 mg of propyl gallate (Example 40), 0.284 mg of 2,5-diethylhydroquinone (Example 41), or 0.284 mg of α-tocopherol (Example 42).

The content of impurities in the mixture obtained in the above was determined in the same manner as in Example 1. As a result, it was confirmed that the content of impurities in the mixture was detection limit or less.

A screw tube was charged with the mixture obtained in the above. This screw tube was allowed to stand in a thermostatic oven of 80° C. for 308 hours, to carry out an accelerated deterioration test of the mixture. Thereafter, the mixture was analyzed by gas chromatography, to determine the content of impurity X denoted by arrow A in FIG. 2(b) in the mixture.

Also, in Comparative Example 6, 4-benzoxy-2,2,6,6-tetramethylpiperidine-1-oxyl, which was used in Example 31, was not used, and only 20 g of 1,2-hexanediol was used. The content of impurities in this 1,2-hexanediol was determined in the same manner as in Example 1. As a result, it was confirmed that the content of impurities was detection limit or less.

Next, an accelerated deterioration test of the 1,2-hexanediol was carried out for 308 hours. Thereafter, the 1,2-hexanediol was analyzed by gas chromatography, and the content of impurity X in the 1,2-hexanediol was determined.

Incidentally, the mixture or 1,2-hexanediol was analyzed by using a gas chromatography analyzing apparatus commercially available from Shimadzu Corporation under the product number of GC-2010 (column: Phenomenex ZB-5 having a diameter of 0.32 mm, a length of 30 m and a film thickness of 1.0 μm), and the content of impurity X in the mixture or the 1,2-hexanediol was obtained from the equation:

$$[\text{Content of impurity } X(\text{ppm})] = \left\{ \frac{[\text{Area of impurity } X \text{ in gas chromatography}]}{[\text{Area of 1,2-hexanediol in gas chromatography}]} \right\} \times 10^6.$$

As a result, the content of the impurities in the mixture after the accelerated deterioration test was detection limit or less in Example 31, detection limit or less in Example 32, detection limit or less in Example 33, 6 ppm in Example 34, 133 ppm in Example 35, 209 ppm in Example 36, 330 ppm in Example 37, 444 ppm in Example 38, 521 ppm in Example 39, 651 ppm in Example 40, 862 ppm in Example 41, and 1688 ppm in Example 42, whereas in Comparative Example 6, the content of the impurities was 2095 ppm. From these results, it can be seen that according to each Example, generation of impurities is more efficiently inhibited as compared with Comparative Example 6. Among those examples, when a phenolic radical scavenger, a tetramethylpiperidineoxyl radical scavenger or an amine radical scavenger is used as a radical scavenger, it can be seen that generation of impurities is more efficiently inhibited as compared with the other Examples and Comparative Example 5. In particular, when the tetramethylpiperidineoxyl radical scavenger or the amine radical scavenger is used as a radical scavenger, it can be seen that generation of impurities is furthermore efficiently inhibited as compared with the other Examples and Comparative Example 6.

From the results as mentioned above, nevertheless a 1,2-alkane polyol having 4 to 18 carbon atoms, which is poor in chemical stability and apt to be deteriorated, is used in the 1,2-alkane polyol-containing composition of the present invention, deterioration of the 1,2-alkane polyol with the passage of time is inhibited. Therefore, it can be seen that the 1,2-alkane polyol-containing composition can be suitably used as, for example, a raw material of cosmetics, an ink for inkjet printers, a fiber, a coating material such as a paint, and the like.

Preparation Examples of cosmetics, in which the 1,2-alkane polyol-containing composition of the present invention is used, are described below. Incidentally, the following "%" is intended to mean "% by mass" in all cases.

Preparation Example 1 (Skin Lotion)

| Preparation Example 1 (skin lotion) | |
|---|---|
| 1,2-hexanediol | 5.0% |
| glycerol | 5.0% |
| oleyl alcohol | 0.1% |
| polyoxyethylene(15) lauryl alcohol ether | 1.0% |
| ethanol | 10.0% |
| perfume | appropriate amount |
| purified water | 79.9% |
| Preparation Example 2 (milky lotion) | |
| 1,2-octanediol | 6.0% |
| dimethicone | 5.0% |
| cyclomethicone | 5.0% |
| liquid paraffin | 4.0% |
| carboxylvinylpolymer | 0.15% |
| sodium hydroxide | appropriate amount |
| perfume | appropriate amount |
| purified water | 79.85% |
| Preparation Example 3 (hair foam) | |
| Ingredients of formulated concentrate | |
| 1,2-pentanediol | 8.0% |
| polyoxyethylene hardened castor oil | 0.1% |
| dimethicone | 5.0% |
| ethyl alcohol | 15.0% |
| perfume | appropriate amount |
| purified water | 71.9% |
| Ingredients for filling | |
| the above-mentioned ingredients of formulated concentrate | 90.0% |
| liquefied petroleum gas | 10.0% |

The invention claimed is:

1. A 1,2-alkane polyol-containing composition used in cosmetics, an ink for inkjet printers, a raw material for fibers or a coating material, wherein the 1,2-alkane polyol is a 1,2-alkane polyol having 4 to 18 carbon atoms, and wherein the composition comprises a tetramethylpiperidineoxyl radical scavenger.

2. A 1,2-alkane polyol-containing composition, wherein the 1,2-alkane polyol is a 1,2-alkane polyol having 4 to 18 carbon atoms, wherein the composition comprises a radical scavenger selected from the group consisting of a tetramethylpiperidineoxyl radical scavenger, a quinone radical scavenger, an amine radical scavenger and a phenothiazine radical scavenger, and wherein the 1,2-alkane polyol-containing composition is suitable as a raw material for fibers or a coating material.

* * * * *